United States Patent [19]
Ernst

[11] Patent Number: 5,571,954
[45] Date of Patent: Nov. 5, 1996

[54] ELECTRICAL RESISTANCE HARDNESS TESTER FOR METALLIC MATERIALS

[76] Inventor: Alfred Ernst, Via Ronchetto, 3, Cadenpino, Switzerland, CH-6814

[21] Appl. No.: 433,446
[22] PCT Filed: Aug. 30, 1994
[86] PCT No.: PCT/EP94/02867
§ 371 Date: May 9, 1995
§ 102(e) Date: May 9, 1995
[87] PCT Pub. No.: WO95/07454
PCT Pub. Date: Mar. 16, 1995

[30] Foreign Application Priority Data

Sep. 10, 1993 [IT] Italy ................... VA93A0018

[51] Int. Cl.⁶ .................. G01N 3/42; G01N 27/04
[52] U.S. Cl. .................. 73/81; 73/85; 324/693
[58] Field of Search ................ 73/78, 81, 85; 324/693

[56] References Cited

U.S. PATENT DOCUMENTS

| | | | |
|---|---|---|---|
| 1,781,002 | 11/1930 | Esnault-Pelterie | 73/81 |
| 4,445,367 | 5/1984 | Goldsmid | 73/81 |
| 4,984,453 | 1/1991 | Enomoto | 73/81 |
| 5,313,825 | 5/1994 | Webster et al. | 73/81 |

FOREIGN PATENT DOCUMENTS

| | | |
|---|---|---|
| 0034807A1 | 9/1981 | European Pat. Off. |
| WO86/06833 | 11/1986 | WIPO |
| WO88/03644 | 5/1988 | WIPO |
| WO92/08119 | 5/1992 | WIPO |

OTHER PUBLICATIONS

*Physics and Technology of Semiconductor Devices*, Italian Edition pub. 1981; Edited, Franco Angeli, p. 25.
Derwent Publications Ltd., London, GB; Class S02, AN 85-091843 C15 (Abstract) Sep. 23, 1984.

Primary Examiner—Thomas P. Noland
Attorney, Agent, or Firm—Pollock, Vande Sande & Priddy

[57] ABSTRACT

A conducting tip of a hardness tester for metals, alloys and similar conducting materials is set forth. The tester comprises a resistance measuring circuit for measuring the resistance between the indenting tip and the test specimen when a certain load is applied to the indenter, made of a substantially insulating material with a superficial conducting film, the conductivity of which decreases toward the tip vertex. This contains the error induced by differences in temperature affecting the resistivity of the conducting superficial film. A tip of conical form with an angle which does not exceed 110 degrees increases precision, as compared with indenters constructed to the Vickers pyramid standard or to the Rockwell 120 degree cone.

6 Claims, 1 Drawing Sheet

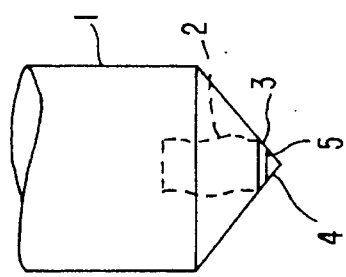
FIG. 1
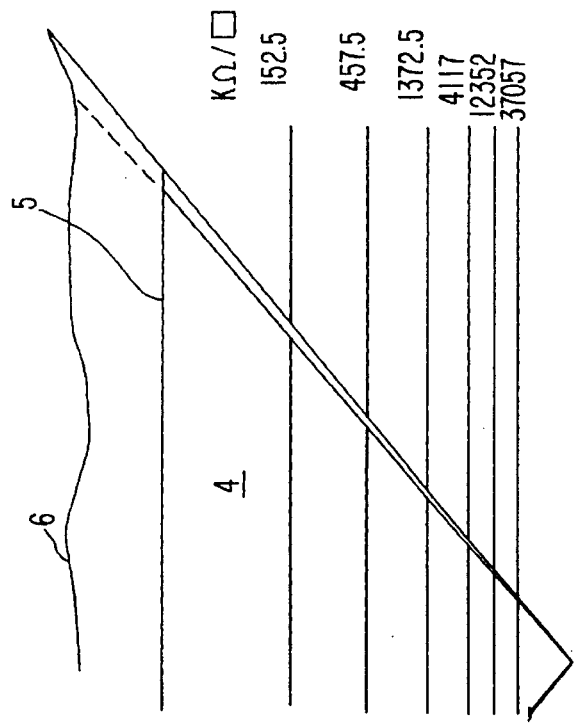
FIG. 2
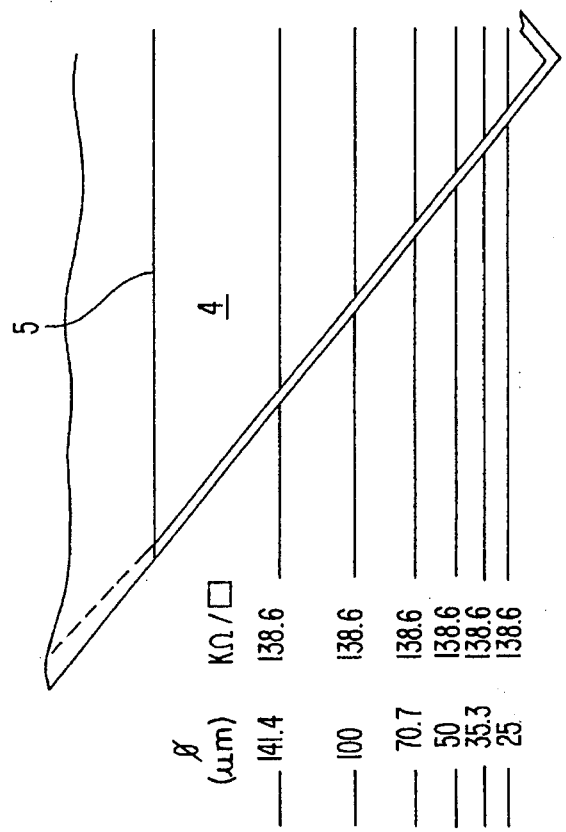

ELECTRICAL RESISTANCE HARDNESS TESTER FOR METALLIC MATERIALS

FIELD OF THE INVENTION

This invention concerns a hardness tester for metals, metal alloys, and other electrically conducting materials, in which a "contact resistance" between the test specimen and an indenting tip loaded with a known force is measured. Its aim is to determine—by comparison or calculation—the hardness of the material which can be expressed in Vickers or Brinell points, or by reference to other standard scales.

BACKGROUND OF THE INVENTION

In the past, there have been many attempts to develop a system for measuring hardness which would not require the observation/measuring of the indentation produced by an indenting tip. In the publication of the International Patent application No. WO-A-86/06833, a method is described for determining hardness by measuring the electrical contact resistance between the indenting tip of a hard and semiconducting material and a test specimen. This method requires the measurement of a contact resistance after having created an electrical discharge between the indenting tip and the metallic test specimen. The most suitable material indicated for this semiconducting indenting tip is silicon carbide. However, this method is not fully reliable due to the variability of tip material resistivity to changes in temperature. Furthermore, it is strongly affected by the contact conditions between the test specimen and the indenting tip. In a successive publication, WO-A-88/03644, a new device and method aimed at overcoming the problems denounced by the method of the earlier publication were illustrated. In this new method only a band, or a geometrically defined sector of the indenting tip surface was made conductive, either by depositing a conducting film, or by implanting specific ionic impurities into the tip material defined areas of the surface. The hardness was substantially determined as a function of the required load necessary to make the indenting tip penetrate the test specimen deep enough to establish an electrical contact with the conducting parts of the tip surface, connected to a measuring circuit. The defined areas of the tip surface were made conductive either by implanting impurities into them, or by depositing a conducting film on these specific areas, as for example, a titanium nitride film. This hardness measuring method is of the "run-length limited" type. In this method, the moment for reading the load applied to the indenter is set when an electrical continuity between the test specimen and the indenter occurs. However, the plastic deformation characteristics of the material affect the flowing of the plastically deformed material along the indenting tip sides introducing errors which are difficult to control. Therefore, even a small inclination of the incidence axis of the indenting tip with respect to the test surface can alter the measurement.

An intrinsically more reliable method for determining hardness, through the measurement of contact resistance, was put forward in an earlier Italian Patent Application No. 83639 A/90 filed on the 24th Oct. 1990 by the present applicant himself (which then brought about the International Publication No. WO 92/08119). According to that method, the hardness of a metallic piece is determined on the basis of the ratio between the contact resistance on a sample of known hardness characteristics, and that on the test specimen, at one, or preferably more, levels of loading. The indenting tip may be a IIp diamond, or other material of adequate electrical conductivity. In the corresponding International Patent Application (WO 92/08119), the use of a diamond tip preimplanted (bombarded) with accelerated nitrogen ions for creating a superficial film or "skin" of adequate conductivity, is described.

The practice of making the measurements after the application of an oil film onto the metallic surface, and the peculiar method for determining hardness—by comparing the readings on a standard material with that on the test specimen—provides an acceptable rate of reproducibility and reliability of the measurements. Nevertheless, the electrical conductivity of a superficial film implanted on a diamond crystal strongly depends on temperature. This remains a problem which is particularly felt in the case of a hardness tester to be used "in the field".

SUMMARY OF THE INVENTION

The main scope of this invention, therefore, is to provide a hardness measuring device based on the measurement of the contact resistance between the indenting tip and the test specimen, which will not be severely affected by temperature differences.

DESCRIPTION OF THE INVENTION

A diamond tip or other hard crystal is implanted superficially so as to create a semiconducting film and the implantation is graduated or otherwise controlled in order to determine a nonuniform conductivity of the implanted superficial film, with a conductivity that gradually decreases towards the vertex of the point. Such an indenting tip was found to maintain the error, due to temperature dependence of the semiconducting superficial film resistivity, within acceptable limits even for an use "in the field" of the hardness tester, where the control of the temperature and/or of test conditions would not allow to otherwise contain measurement errors. The conductivity of the superficial film, however, must not be uniform—either by graduating the implantation or by other means—it must steadily decrease towards the vertex of the indenting tip.

In practice, hardness measuring errors, in terms of Brinell or Vickers points, can be contained within ±2%.

The square resistivity ($\Omega$/square) of the superficial film implanted on the indenting tip lies between a peak value near the tip vertex, which is normally between 10,000 and 50,000 K$\Omega$/square, and a minimum value at the base of the implanted tip cone or pyramid, normally between 50 and 1000 K$\Omega$/square. In practice, the difference in the film resistivity between "base" and "vertex" of the tip portion which is going to indent the test specimen, should be of at least one order of magnitude.

The resistivity of the superficial film implanted in this "operative" zone of the tip can vary in a substantially linear manner. However, due to the hardness determination method which compares the contact resistance value of a reference sample with that of the test specimen, the incidence on the hardness determination precision, due to deviations from linearity of the law of variation of the implanted film resistivity along the indenting vertex portion of the tip, is relatively small.

In other words, whilst, to reach the set objectives, it is essential that the resistivity of the implanted film should vary from a minimum value at the "base" of the electrical contact of the indenting tip operating portion, to a maximum value near the tip vertex, the manner in which this variation develops along the implanted surface of the tip vertex operational portion, is not particularly important. Actually, it can be rather distant from linearity and may even be non-linear at all. However, it is preferable to avoid sharp "steps" in the resistivity variation of the film.

Normally, the diamond is solidly set onto the vertex of a metallic indenter and is then ground to the required conical shape. The indenting tip thus prepared can be submitted to one or more ionic implantation and "tempering" treatments in order to "precondition" the crystal, and/or to give it a certain basic superficial conductivity. During this treatment, the operational part of the diamond point vertex may also be screened from the ionic bombardment, by covering it with a drop of resin or other shielding material.

A final implantation of the operational part of the tip vertex is therefore carried out under controlled dosage and acceleration energy conditions, using "baffles" in the accelerated ion stream, so that the dose is graduated and decreases steadily towards the vertex of the indenting tip. The implantation can also be carried out in a uniform manner, followed by a tip treatment so that the conductivity of the surface induced by the implanted ions is progressively reduced towards the vertex. This can be done, for example, through differential thermal treatment by laser, or by "lapping" the tip in a gradually increasing way from the base to the vertex.

The tip is preferably a diamond, and its final implantation is carried out by ionic bombardment with accelerated nitrogen atoms. The implantation may lie between $1 \times 10^{15}$ and $1 \times 10^{17}$ nitrogen atoms/cm$^2$ approximately, whereas the implantation energy may lie between 50 and 200 KeV.

Naturally, the above implantation values are average values. In order to obtain a graduation of the resistivity of the superficial film implanted with nitrogen atoms, the implantation must be carried out using appropriate mobile screens, or baffles, to direct the accelerated ion stream, so that the implanted dose is progressively reduced towards the indenting tip vertex.

Alternatively, the required resistivity graduation can be obtained by a uniform implantation of the indenting tip vertex, followed by a "lapping" treatment more marked at the vertex and gradually decreasing in intensity as the distance from the tip vertex grows. The effectiveness of the invention is due firstly to the fact that by using a tip of a superficially implanted material which is intrinsically non-conductive, for example diamond, the "contact resistance" that is measured is substantially the sum of two components. The first of these components is due to a real contact resistance between the metallic material indented by the tip and the indenting portion of the tip. The second is due to the electrical resistance offered by the implanted superficial film of the tip, from the contact area between the tip and the metallic test material to the metallic body of the indenter, which is electrically connected to the circuit for measuring the "contact resistance". The first component is substantially negligible, compared with the second. In other words, the "contact resistance" that is measured, actually represents the resistance of the implanted tip semiconducting film between the limit of the indented zone of the metallic material (contact zone metal/tip) and the base of the implanted portion of the tip vertex which is in contact (set into, or anyway electrically connected through a low resistance path) with the highly conducting indenter body. Also after these considerations, it is clear that the measured "contact resistance" is always an inversely proportional indication of the degree of penetration of the indenting tip into the metallic test specimen, under the specific load conditions applied to the indenter. In the case of a film implanted uniformly, and in such a way as to produce a uniform resistivity of the conducting film, there is a measuring situation such that to a "doubling" of the hardness (corresponding to approximately a halving of the indentation area, which in the case of a loaded tip corresponds to a reduction of the indentation diameter by $\sqrt{2}$), corresponds a difference of contact resistance ($\Delta R$) that remains almost constant. This means that the error due to the dependence of the resistance on the temperature is considerably magnified when one measures hard materials, or makes measurements at relatively low loads. In other words, the influence of the temperature on the resistance values measured, remains constant, but in the case of comparative measurements of high hardness, or measurements carried out at relatively low loads, it has a marked weight on the measurement and induces an excessive error in the hardness measurement, expressed for example in Vickers points.

Viceversa, using an indenting tip made according to this invention, with a conducting superficial film having maximum resistivity near the vertex and decreasing towards the base of the operating zone, which indent the test specimens, electrically connected through the conducting body of the indenter, the variation of resistance measured when the indentation area is doubled or halved (i.e. when the hardness is about halved or doubled) is no longer constant, but decreases gradually from a peak differential value—when the diameter or width of the indentation is small (corresponding to the vertex portion of the implanted part of the tip with higher resistivity)—as the indentation diameter or width increases (corresponding to the zones of the conducting film near the base of the operational zone of the implanted diamond tip vertex, which has a much lower resistivity than that measured near the tip vertex). In this way, the error due to the (constant) temperature effect on the implanted film resistivity can be contained within acceptable limits such as those regarding relatively low hardness levels, or measurements made with (higher) other loads (wide indentations).

Even though pyramidal forms could theoretically be used, the conical form was found to be the most suitable one.

Another aspect of the invention is that to obtain reproducible electrical resistance values it is very important that the angle formed between the surfaces of a the indenting tip and of the test specimen be sufficiently large, and decidedly greater than that which is formed with indenting tips of standardized form.

The Rockwell conical diamond indenter has a cone angle of 120°, which creates an angle between the test specimen surface and the indenter surface of 30°, which is too small to obtain a well-defined electrical contact. The use of indenters of standardized form was thus abandoned. Conical indenters with a smaller angle are now used, particularly when a perfect perpendicularity of the indenting tip load axis to the test surface cannot be ensured. This may often occur when surfaces with a complex form are tested, such as the flanks of helicoidal toothings, or internal surfaces which are difficult to reach, and even more, in the case of hand operated "field" instruments.

All these problems about measurements reproducibility are surprisingly reduced, or may even disappear, when a conical indenter tip, with an angle subtending the vertex of 110° or less, is used. A certain radiusing of the tip to prevent fragility is acceptable, but this must be a function of the minimum load and the maximum hardness with which one wishes to work, as it is only the contact on the conical part which ensures a well-defined reproducibility. Once this criterion is satisfied, the greater the radius the less fragile the tip of the indenter is, and the easier the grinding of the cone.

This result has been confirmed in all hardness test conditions based on the measurement of an "electrical contact resistance" between an indenting tip and a conducting test specimen and not only in the case of tips with graduated resistivity.

The ability of a conical tip of not more than 110° to ensure measurement reproducibility of an "electrical contact resistance" seems to be independent of the means by which that resistance is created. The reduced angle conical tip is in fact primarily effective in ensuring the reproducibility of the indentation surface even when the loading axis is slanted several degrees (up to 6°) with respect to the axis perpendicular to the test specimen surface. This is extremely useful in the cases of field measurements made by manual loading the indenter.

DESCRIPTION OF THE FIGURES

FIG. 1 is a schematic view of an indenter with conical diamond tip, having an angle subtending the vertex of 100°, according to first aspect of this invention;

FIG. 2 is a drawing showing a comparison between the operative vertex part of a diamond tip a) implanted uniformly; b) implanted in a graduated manner, as according to this invention.

DESCRIPTION OF THE PREFERRED EMBODIMENT

With reference to FIG. 1, an indenter (1) comprises a diamond crystal (2) (or other equivalent material), firmly set onto the extremity of the indenter point using well-known techniques. The tip is then ground to the required conical shape, with an angle subtending the vertex of 100°. The tip (3) of the diamond (3) can protrude for one or more millimeters from the metallic (1) body of the indenter point. The operative part (4) of the diamond tip, that is the part of the vertex which will indent a metallic test specimen under an axial load applied to the indenter, is normally a portion of the ground point of the diamond that protrudes from the metal body (1). Depending on the load applied, and the hardness of the material used, the operative part (4) of the diamond can protrude axially from a few hundredths of a millimeter up to a few millimeters.

A conducting lacquer film, or a conducting coating may be formed so as to extend from the operative part base line (5) of the tip vertex to the metal body of the indenting tip (1). In this way, the electrical resistance of the "connecting" path from the operative part of the tip to the circuit for measuring the contact resistance between the indenting tip and the conducting test specimen, may be made substantially negligible.

A partial cross-section of the vertex operative part of a tip made according to this invention, and a similar cross-section of a tip implanted uniformly, according to the prior technique, are outlined in FIG. 2. As an example, the respective square resistivity values (KΩ/square) of the implanted superficial film of the conical crystal surface, at various levels, marked with the indication of the diameter (ϕ) of the cone (expressed in μm) are shown in FIG. 2.

In the drawing, the superficial film of the diamond tip, made semiconductive by ionic implantation of accelerated nitrogen atoms, is schematically shown by the darkened "skin" portion. In the case of a uniform implantation this is schematically shown with a constant thickness, whereas in the case of a tip made according to this invention it is schematically shown with a thickness that decreases towards the vertex.

In both cases, the operative portion of the tip vertex is electrically connected to a resistance measuring circuit by a conducting film (6) formed on the implanted crystal tip, from the base level (5), which defines the limits of the tip's working (operative) zone, and which extends to the indenter's metal body of the hardness measuring instrument.

The instrument and the measuring method can be similar to those described and illustrated in the already mentioned International Patent Application, Publication No. WO A 92/08119, which corresponds to the European Patent Application No. 91918395.4/0506917, the contents and illustrations of which are expressly incorporated herein.

EXAMPLE

An instrument device substantially similar to that described and illustrated in the above publication of European Patent No. 0506917, alternatively provided either with a tip (A), implanted uniformly, as schematically shown on the left in FIG. 2, or a tip (B), implanted in a graduated manner according to this invention as schematically shown on the right in FIG. 2, has been used to compare the results obtained with each.

Both tips were conical, with a vertex angle of 100°, and had a tip radius of about 0.01 mm. The operative part of each tip vertex (for a height of 1.5 mm) had been implanted with nitrogen at an average dose of $4 \times 10^{15}$ atoms/cm$^2$ with an energy level of 150 KeV. The tip (A) had a uniform resistivity of the superficial film of around 138 KΩ/square. The tip (B) had been successively lapped to produce a graduated resistivity characteristic, approximately as shown in FIG. 2, and namely:

the resistivity at the vertex was:≈37,000 KΩ/square the resistivity near the base line of the electrical connection, at 0.08 mm from the geometric vertex was:≈52 KΩ/square The resistivity of the implanted superficial film was reduced approximately by ⅓ for every doubling of the indentation area.

Trials carried out on steel test specimens, at different temperatures and loads, causing indentations of different diameters, and using the same specimens of known hardness as references, gave results from which the series of correspondence values shown in the following table could be extrapolated:

| Indentation diameter | Vickers hardness values according to different loads | | | | | Percentage error found for a temperature variation of ±3° C. | |
| --- | --- | --- | --- | --- | --- | --- | --- |
| nm | 10 kg | 5 kg | 2 kg | 1 kg | 0.5 kg | Tip A | Tip B |
| 141,4 | 440 | 220 | 88 | 44 | | ±1.3 | ±1.2 |
| 100 | 880 | 440 | 176 | 88 | 44 | ±2.8 | ±1.2 |
| 70,7 | | 880 | 352 | 176 | 88 | ±4.4 | ±1.2 |
| 50 | | | 704 | 352 | 176 | ±5.6 | ±1,2 |
| 35,3 | | | | 704 | 352 | ±7.0 | ±1,2 |
| 25 | | | | | 704 | ±8.4 | ±1,2 |

I claim:

1. A hardness tester for metals, metal alloys and similar conducting materials, comprising an indenter provided with an electrically conducting indenting tip and with means for measuring the resistance between said tip and a test specimen under a certain load applied to the indenter, said tip being made of a substantially insulating material having a conducting superficial film, the conductivity of which decreases towards the tip vertex.

2. A hardness tester as described in claim 1, wherein said conducting superficial film is produced by ionic implantation.

3. A hardness tester as described in claim 1, wherein the square resistivity ($\Omega$/square) of said conducting superficial film decreases from a value ranging between 10,000 and 50,000 K$\Omega$/square near the tip vertex, to a value ranging between 50 and 1,000 K$\Omega$/square at an electrical connection base of the implanted operative part of the tip vertex in a resistance measuring circuit.

4. A hardness tester as described in claim 1, wherein said tip is made of diamond implanted with an average dose of nitrogen ranging between $1 \times 10^{15}$ and $1 \times 10^{17}$ atoms/cm$^2$ at an energy level ranging between 50 and 200 KeV.

5. A hardness tester as described in claim 1, wherein its tip is conical.

6. A hardness tester according to claim 1, wherein said tip is conical and subtends a vertex angle equal to or less than 110°.

* * * * *